United States Patent
Smeets et al.

(12)
(10) Patent No.: US 6,521,591 B1
(45) Date of Patent: Feb. 18, 2003

(54) PHARMACEUTICAL COMPOSITION FOR MUSCULAR ANABOLISM

(75) Inventors: Rudolf Leonardus Lodewijk Smeets, Venlo (NL); Robert Johan Joseph Hageman, Waddinxveen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/500,802

(22) Filed: Feb. 10, 2000

(51) Int. Cl.$^7$ .............................................. A61K 38/00

(52) U.S. Cl. .............................. 514/2; 514/23; 514/54; 514/60; 514/574; 514/578; 514/634; 514/665; 424/439; 530/380; 530/360; 530/399; 530/832; 530/829; 530/833

(58) Field of Search ................................ 514/2, 23, 54, 514/60, 574, 578, 634, 665; 530/380, 360, 399, 832, 829, 833; 424/439

(56) References Cited

U.S. PATENT DOCUMENTS 5,036,052 A * 7/1991 Ozeki et al. ................... 514/19
5,726,146 A * 3/1998 Almada et al. ................ 514/2

FOREIGN PATENT DOCUMENTS

| EP | 0 875 155 A1 | 11/1998 |
| WO | 99/64022 | 9/1992 |
| WO | 98/43617 | 10/1998 |
| WO | 9956758 | * 11/1999 |

* cited by examiner

*Primary Examiner*—Marianne C. Seidel
*Assistant Examiner*—C. Delacroix-Muirheid
(74) *Attorney, Agent, or Firm*—Young & Thompson

(57) ABSTRACT

A pharmaceutical composition suitable for enhancing muscular anabolism contains, per daily dose, at least 5 mg of anabolic initiators comprising anabolic growth factors, at least 0.12 g of protein equivalents of anabolic substrates and at least 3 g of anabolic facilitators comprising at least 1 g of creatine or its functional analog. The anabolic initiators may be derived from a non-denatured animal protein, non-denatured being defined as having an $F_0$ of less than 3.0.

13 Claims, No Drawings

PHARMACEUTICAL COMPOSITION FOR MUSCULAR ANABOLISM

FIELD OF THE INVENTION

The invention is concerned with pharmaceutical or nutritional compositions suitable for increasing muscular mass ("lean body mass"), e.g., for athletes, and for preventing loss of lean body mass that may occur in periods of rest and during recovery from disease.

BACKGROUND

Products intended for increasing muscle mass are commercially available, such as the product PHOSPHAGAIN (a creatine containing supplement). A review of nutritional supplements for increasing muscle mass has been presented by Clarkson and Rawson in *Crit. Rev. Food Sci. Nutr.* 39 (1999) 317—328. They conclude that many claims of this effect are unsupported, and that the weight gain following of creatine ingestion is most likely water retention but that it could also be due to some new muscle protein. From this review, we learn that very little evidence exists that ergogenic components indeed improve athletic performance.

According to U.S. Pat. No. 5,726,146, lean body mass can be increased without increase body fat by administration of a supplement containing creatine, taurine, and ribonucleic acid, optionally with carbohydrate for enhancing cellular uptake of these ingredients.

WO 98/43617 discloses a dietary supplement comprising L-carnitine, coenzyme Q10 and taurine useful in the correction of the abnormality in mitochondrial energetics occurring in cardiac failure and certain other diseases. It further discloses a high protein, high calorie nutritional feeding supplement comprising these three nutrients together with cysteine, vitamin E, vitamin C, selenium, and thiamin. The protein fraction can comprise of normal (i.e. denatured) whey proteins, 1:1 with casein.

WO 95/10192 discloses a nutritional drink containing colostrum, for the purpose of improving physical performance and recovery. The colostrum is defatted and decaseinated, and sterilized by filtration.

WO 99/56758 describes a food composition for use in changing body composition (increased lean tissue) and/or physical work capacity, which contains undenatured colostrum, in particular colostrum derived growth factors and colostrum-derived casein. The composition may further contain vitamins minerals, amino acids, and carbohydrates.

There is a need for a nutritional and/or pharmaceutical preparation that indeed helps to increase muscle strength during training. During periods when training efforts have to be stopped, e.g. because of injuries or holidays, it is frequently observed that muscle mass that was built up during exercise rapidly decreases, and a lot of time is normally required to regain the level that was previously present. Losses in lean body mass are also observed frequently in persons that have to be inactive for quite a while, e.g. because they have to stay in bed to injury, disease or other disorders. Thus, there is also a need for effective formulations, and especially nutritional formulations, that help prevent losses of body mass during these periods.

Muscle consists of proteins, like myosine and actin, lipids and carbohydrates. Skeletal muscle tissue is continuously broken off and replaced in a dynamic process that depends on mechanical damage, exercise and feeding status at a particular point in time.

DESCRIPTION OF THE INVENTION

It has now been found that the simultaneously or sequential administration of
1-component that triggers anabolism (initiators),
2-components that provide building blocks (substrates) for biosynthesis of muscle tissue, and
3-components that facilitate biosynthetic processes (facilitators) increases, for a certain period of time, lean body mass and/or can prevent catabolism in periods of rest.

Sequential use means that the different components can be administered separately during the day, but they must be consumed during the same day. In this way, for example a product with one or more facilitators is consumed first, followed by consumption, e.g. 2 hours after consumption of the first product, of an effective amount of substrate and initiator in the same product. However, preferably all three types of components are consumed simultaneously in one product.

The invention pertains to pharmaceutical and/or nutritional compositions suitable for enhancing muscular anabolism, i.e. production of muscle tissue or reduction of loss of muscle tissue. The compositions according to the invention comprise an initiator for muscular tissue production, a facilitator for biosynthesis, and a substrate. They furthermore comprise a facilitator, including creatine or a functional equivalent, and optionally further components facilitating tissue production, and also a substrate comprising e.g. carbohydrates, amino acids etc.

The products can have a powdered structure, packed in sachets or cans or similar reservoirs. Other dry forms that are equally suitable are cereals and bars. The product can also have the form of a drink, e.g., based on a dairy drink (mil, whey) or fruit juice (orange, apple, grape). For liquid products it is advantageous to let it have a pH below 4.2 in order to stabilize some of the active components. The product can also have the form of a paste or spread or sauce.

Initiators

The initiators (also referred to as triggering substances or triggers) to be used in the compositions of the invention are components that start up the anabolic processes. Examples are anabolic growth factors like Insulin-Like Growth Factor (IGF-1). These must be present as part of an extract of a protein-rich food ingredient, in particular in an extract from a proteinaceous material of animal origin, like mil, blood or egg. Undenatured whey and especially undenatured colostrum in particular bovine colostrum comprises a variety of anabolic trigger substances. The high effectivity of whey and colostrum that was found may also be explained by the presence of components that increase the bioavailability of the initiator components. In case of anabolic growth factors, such components are binding proteins.

Specific extracts of animal origin may be used as a source of triggers for anabolism, providing that the extraction procedures do not affect the trigger components. The $F_0$ value, defined in the Manual of Common Methods, defines decimal reductions of germs as a result of heat treatment of food products. Thus an $F_0$ value of 3.0 defines a thousand-fold reduction of germs and is achieved by treatment at 121° C. with a Z value of 10. A heat treatment above $F_0=3.0$ normally destroys most of these trigger components. Thus the extracts should not have been subjected to a heat treatment with an $F_0$ of 3.0 or higher, and preferably any heat treatment should have an $F_0$ of less than 2.4. Most preferably, a heat treatment, if any, should not have a $F_0$ of more than 0.2.

Suitable methods for obtaining such products avoiding substantial heat treatment are described in the art and include filtration and centrifugal techniques. The amount of extract can be as low as 5 mg per daily dose, if a high degree of purification of the triggering substances from the proteinaceous material is obtained. However, when bovine colostrum is used as sole source for triggering substances, at least 5 g of the product, that is obtained by using the method disclosed in WO 97/16977, should be included in a daily dose according to the invention.

The inclusion of insulinotrohic components like digestible carbohydrates and arginine and lysine can further enhance the triggering activity of extracts of animal proteins. Arginine and lysine should be included in amounts of more than 1.0 g and preferably more than 1.5 g per daily dose. Carbohydrates are preferably glucose polymers like maltodextrines and should be present in an amount of more than 4 g and preferably more than 8 g.

Substrates

In order to allow an adequate rate of biosynthesis of muscle tissue, the presence of sufficient amounts of substrate in the form of a variety of amino acids is required. It appears that requirements for protein in athletes are higher than in non-athletes. Daily requirements in strength athletes are above 120 g protein and in endurance athletes above 100 g protein. Though it appeared that some amino acids become rate-limiting earlier in biosynthesis of muscle tissue than other ones, a mixture of all amino acids, including the essential amino acids is preferably provided according to the invention. These amino acids should be provided as protein or hydrolysate thereof; it is especially preferred to use intact protein for taste reasons and because the amino acids will then be released more slowly. The latter ensures a constant but sufficient provision of the substrate amino acids to the tissues and where the amino acids are insulinotrophic, a longer increase of plasma insulin levels.

In order to provide sufficient amounts of amino acids, typically more than 5 g protein and especially more than 10 or even more than 20 g protein in included in the formulations. Suitable proteins are all proteins that comprise high amounts of essential amino acids, especially leucine, lysine and methionine, such as casein, soy, pea, potato, egg and whey proteins. However, when undenatured proteins of animal origin like colostrum or whey from mammal mil, blood or eggs are used, these ingredients also comprise triggering components for anabolism.

Proteins and amino acids can be expressed as protein equivalents (PE). One PE can be calculated by multiplying the Kjeldahl nitrogen content of the substrate by the factor 6.25.

In order to increase the amount of the amino acids that are most critical to muscle building, methionine, lysine and leucine, additional amounts of these amino acids can be included. This can be done by including peptides, or amino acid complexes or free amino acids in the formula. Preferably free amino acids are used, especially those in the L-form. The amounts of methionine that are included per daily serving should exceed 0.2 g (9.4% N: 0.12 g PE) and preferably exceed 0.5 g; the preferred range is 1–6 g Met. Preferably the amount of methionine is more than 2.8 g per 100 g protein equivalents and in particular in the range 3.0–5.0. The amount of lysine per daily serving should be more than 1.0 g (19.6% N: 1.3 g PE) and preferably more than 2.0 g, e.g. 2.5–15.0 g. Calculated per 100 g protein equivalents, the amount of lysine should be more than 8.3 g, and in particular in the range 8.5–11. The amount of leucine per daily serving should be more than 2.0 g (10.4% N: 1.3 g PE) and preferably more than 3.0 g, e.g. 3.5–20 g.

Sleeping disorders are often experienced, especially in those persons that consume large amounts of branched chain amino acids (BCAA valine, isoleucine, leucine). This is especially undesirable when one wants to maintain anabolism during a longer period of time. For this reason it is important that the ratio of L-leucine/BCAA is relatively high. This ratio should be higher than 0.46 and in particular be in the range 0.5–0.3.

In addition the amount of L-tryptophan should be relatively high. The ratio Trp/BCAA should be higher than 0.055, preferably in the range of 0.06–0.2 and in particular be in the range of 0.07–0.13. Also persons that suffer from disease frequently appear to experience problems with maintaining nitrogen balance. By consuming the abovementioned types and amounts of substrates their capacity to synthesize muscle tissue is maximally supported.

Facilitator

According to the invention, lean body tissue can only be synthesized when sufficient energy is available and sufficient amounts of cofactors are available as facilitator of the anabolic biochemical processes. Intracellular energy should be available in the form of adenosine tri-phosphate (ATP). Creatine phosphate (CP) is able to provide "energized phosphate" to ADP, which restores ATP levels once they have been used for labor or biochemical processes. It is therefore especially advantageous to include in the formulation a source of both energy, in the form of digestible carbohydrates, and creatine. Instead of creatine, Krebs cycle intermediates such as citrate and Krebs cycle precursors, such as pyruvate, glutamate, glutamine, can be used.

The amount of digestible carbohydrates should be above 4 g per daily dose and preferably more than 10 g per day. That of creatine should be above 1.0 g per daily dose and preferably more than 2.0 g, for example 8 g. Suitable carbohydrates are maltodextrines, e.g. the one having DE=19, lactose, sucrose or mixtures thereof. Creatine can be the salt creatine, creatine phosphate, or functional and stable equivalents thereof.

Because of the high amounts of protein that are digested, consumption of extra amounts of minerals and vitamins in the diet is desirable. Especially vitamin B6 should be fortified to ensure to allow a consumption of at least 1.8 mg vit. B6 per 100 g protein that is consumed. The high volume of protein normally consumed by body building ensures a load of methionine that should be handled appropriately in order to have only moderate increases in plasma levels of homocysteine. It is therefore recommended to include folic acid, vitamin B12, vitamin B6, zine and magnesium in the formula, because deficiencies of one or more of these compounds frequently occur, while they are mandatory for homeostasis of homocysteine loads. The levels should be at least 1 mg vitamin B6, 200 µg folic acid, 1 µg cyanocobalamine, 40 mg magnesium and 5 mg zinc or the functional equivalents of these components per daily serving. The prior art discloses which forms of these components can be advantageously used for nutritional purposes. Vitamin B6 can e.g. have the form of principles or pyridoxal; folic acid can be in the monoglutamate form; zinc can be administered as salt, e.g. as zine carbonate; magnesium can have the form of an inorganic salt like magnesium carbonate.

A further improvement of the product can be obtained by including in the product one of the metabolites of leucine, especially beta-hydroxy-beta-methylbutyrate (HMB). The latter compound can be included in an amount of 1–20 g per daily serving, in particular in the range 2–5 per day. The component can be included as pure substance or as inorganic salt such as the calcium salt, or any other functional equivalent. Other components like yeast, carnitine, pyruvate, dihydroxyactone, glutamine, ubiquinone (especially CoQ10) and other vitamins and minerals can be included as well. It is especially preferred to include melatonin, which supports the anabolic function of the composition.

Table 1 shows the scope of the products according to the invention.

TABLE 1

Components according to the invention

| Initiators | Substrates | Facilitators |
| --- | --- | --- |
| Undenatured extracts from proteinacous material of animal origin + optionally extra: insulinotrophic components like: digestible carbohydrates L-Arginine L-Lysine and/or HMB | Proteins and/or L-leucine L-methionine L-lysine | Creatine and/or Krebs cycle intermediates or precursors thereof + optionally digestible carbohydrates + optionally extra: vitamin B6, folic acid, vitamin B12 magnesium, zinc melatonin |

EXAMPLES

Example 1

Bar For Body Building Purposes

An extract for isolating anabolic components from colostrum is prepared by applying the centrifugation process as described in WO 97/16977. The liquid phase is consequently purified by elution over a strong anionic exchanger. The liquid is then freeze-dried. The bar is prepared by using methods that are known in the art that ensure that per bar of 30 g weight is present:

100 mg of colostrum powder produced as given above,
5 g soy protein
2 g L-leucine
1.5 g L-lysine
0.6 g L-methionine
2.0 g creatine
13.6 g glucose syrup
2.0 mg vitamin B6
0.2 g L-tryptphan

Example 2

Powdered formula in can of 900 g. Twenty grams of powder are dissolved in 200 ml milk.
Per 100 g powder the formula contains:
50 g undenatured colostrum powder
40 g maltodextrine DE 19
10 g creatine
Per day about 40–100 g of the powder is consumed.

Example 3

Powder packed as in example 2, consisting per 100 g formula of:

33 g undenatured egg white powder
50 g maltodextrine DE 25
12 g creatine
2 g melatonine
5 g of a mineral/vitamin premix that comprises 1250 ug folic acid, 10 mg pyridoxine, 7.5 ug cyanocobalamine, 75 mg zinc, 10 mg copper and 400 mg magnesium.

Per day about 25 g of powder is consumed e.g. suspended in 200 ml orange juice.

Example 4

Powdered product for body building, that consists per 100 g formula of 72 g undenatured whey protein powder, providing 43 g protein and 21 g lactose
5 g sucrose
8 g creatine
1 g L-methionine
1 g L-tryptophan
1 g melatonin
6 g of the mineral/vitamin premix described in example 3
4 g HMB
4 g L-leucine Per day about 50 g formula is consumed, e.g. by dissolving this amount of powder in milk together with the breakfast cereal.

Example 5

Liquid product obtained by preblending the powder of example 3 in orange juice.

Example 6

Supplement

The following components were combined an the amounts indicated for a daily dose:

30 g bovine colostrum
120 g carbohydrates
5 g creatine
6 g of essential L-amino acids (Lys, Leu, Val, Phe, Thr, His, Ile, Met) methionine module: Zn, Vit. B6, folic acid

Example 7

Supplement

The following components were combined an the amounts indicated for a daily dose:

30 g bovine colostrum
36 g carbohydrates
5 g creatine
6 g of essential L-amino acids (Lys, Leu, Val, Phe, Thr, His, Ile, Met) methionine module: Zn, Vit. B6, folid acid

Example 8

Supplement

The following components were combined an the amounts indicated for a daily dose:

30 g bovine colostrum 6 g carbohydrates 5 g creatine

We claim:

1. A pharmaceutical composition containing, per daily dose:
   - at least 5 mg of anabolic initiators comprising anabolic growth factors,
   - at least 0.12 g of protein equivalents as anabolic substrates, the protein equivalents comprising a weight ratio of leucine to branched-chain amino acids between 0.5 and 3.0, and
   - at least 3 g of anabolic facilitators comprising at least 1 g of creatine or its functional equivalent.

2. The pharmaceutical composition of claim 1, wherein the anabolic initiators comprise at least 5 g of a non-denatured animal protein, non-denatured being defined as having an $F_0$ of less than 3.0.

3. The pharmaceutical composition of claim 2, wherein the animal protein is selected from milk protein, egg protein and blood protein.

4. The pharmaceutical composition of claim 3, wherein the animal protein comprises colostrum.

5. The pharmaceutical composition of claim 1, comprising digestible carbohydrates at a level of at least 4 g per daily dose.

6. The pharmaceutical composition of claim 5, comprising digestible carbohydrates at a level of at least 8 g per daily dose.

7. The pharmaceutical composition of claim 1, comprising total proteins at a level of more than 10 g per daily dose.

8. The pharmaceutical composition of claim 1, comprising one or more of the following per daily dose: more than 0.2 g methionine, more than 1.0 g lysine, more than 2.0 g leucine, and more than 0.2 g tryptophan.

9. The pharmaceutical composition of claim 8, in which the weight ratio of tryptophan to branched-chain amino acids is between 0.055 and 0.2.

10. The pharmaceutical composition of claim 1, further comprising at least one component selected from the group consisting of vitamin B6, vitamin B12, folic acid, magnesium and zinc.

11. The pharmaceutical composition of claim 1, further comprising 1–20 g of β-hydroxy-β-methylbutyrate and/or 0.5–10 g melatonine per daily dose.

12. The pharmaceutical composition of claim 1, which is a supplement.

13. A method of improving muscular anabolism, comprising:
   administering to a subject in need of muscular anabolism an effective amount of
   - at least 1 g of biosynthese facilitators,
   - at least 5 g of non-denatured animal protein per day, and
   - at least 0.12 g of protein equivalents as anabolic substrates, the protein equivalents comprising a weight ratio of leucine to branched-chain amino acids between 0.5 and 3.0.

* * * * *